United States Patent [19]

Merger et al.

[11] Patent Number: 4,713,476

[45] Date of Patent: Dec. 15, 1987

[54] PROCESS FOR THE PREPARATION OF ALIPHATIC DI- AND POLYURETHANES

[75] Inventors: Franz Merger, Frankenthal; Friedrich Towae, Ludwigshafen, both of Fed. Rep. of Germany

[73] Assignee: BASF Aktiengesellschaft, Ludwigshafen, Fed. Rep. of Germany

[21] Appl. No.: 879,025

[22] Filed: Jun. 26, 1986

Related U.S. Application Data

[63] Continuation-in-part of Ser. No. 135,247, Mar. 31, 1980.

[30] Foreign Application Priority Data

Apr. 30, 1979 [DE] Fed. Rep. of Germany ....... 2917493

[51] Int. Cl.$^4$ ........................................ C07C 125/073
[52] U.S. Cl. ........................................ 560/115; 560/25; 560/158
[58] Field of Search ................. 560/24, 115, 157, 158, 560/25

[56] References Cited

U.S. PATENT DOCUMENTS

| | | | |
|---|---|---|---|
| 2,181,663 | 11/1939 | Martin | 260/2 |
| 2,343,808 | 3/1944 | Schlack | 260/2 |
| 2,409,712 | 10/1946 | Schweitzer | 560/157 |
| 2,568,885 | 9/1951 | Dreyfus | 260/77.5 |
| 2,623,867 | 12/1952 | Dreyfus | 260/77.5 |
| 2,653,144 | 9/1953 | Wielicki | 260/77.5 |
| 2,806,051 | 9/1957 | Brockway | 560/24 |
| 2,817,684 | 12/1957 | Bortnick | 260/553 |
| 2,828,291 | 3/1958 | Saunders | 260/77.5 |
| 2,973,342 | 2/1961 | Inaba et al. | 260/77.5 |
| 3,046,254 | 7/1962 | Imaba et al. | 260/77.5 |
| 3,054,777 | 9/1962 | Imaba et al. | 260/77.5 |
| 3,054,819 | 9/1962 | Barclay, Jr. et al. | 260/453 |
| 3,119,793 | 1/1964 | Imaba et al. | 260/77.5 |
| 3,185,656 | 5/1965 | Gabler et al. | 260/30.2 |
| 3,223,682 | 12/1965 | Gablet et al. | 260/77.5 |
| 3,291,763 | 12/1966 | Becalick et al. | 260/13 |
| 3,366,662 | 1/1968 | Kober et al. | 260/453 |
| 3,388,103 | 6/1968 | Imohl et al. | 260/77.5 |
| 3,390,137 | 6/1968 | Kirshenbaum et al. | 260/77.5 |
| 3,412,072 | 11/1968 | Bouboulis et al. | 260/77.5 |
| 3,461,149 | 8/1969 | Hardy et al. | 260/453 |
| 3,467,687 | 9/1969 | Hardy et al. | 260/453 |
| 3,467,688 | 9/1969 | Bennett et al. | 260/453 |
| 3,481,967 | 12/1969 | Ottmann et al. | 260/453 |
| 3,523,962 | 8/1970 | Ottmann et al. | 260/453 |
| 3,734,941 | 5/1973 | Sydor | 260/453 P |
| 3,763,217 | 10/1973 | Brill | 260/471 |
| 3,895,054 | 7/1975 | Zajacek et al. | 260/471 |
| 3,992,430 | 11/1976 | Bacskai | 260/453 |
| 4,081,472 | 3/1978 | Tsumura | 260/453 |
| 4,153,624 | 5/1979 | Fern | 260/453 |
| 4,260,781 | 4/1981 | Harvey | 560/24 |
| 4,310,692 | 1/1982 | Findeisen et al. | 564/61 |
| 4,388,238 | 6/1983 | Heitkamper et al. | 260/239 |
| 4,430,505 | 2/1984 | Heitkamper et al. | 560/24 |

FOREIGN PATENT DOCUMENTS

| | | |
|---|---|---|
| 896412 | 7/1949 | Fed. Rep. of Germany . |
| 528437 | 5/1938 | United Kingdom . |
| 530267 | 6/1938 | United Kingdom . |
| 1025436 | 8/1964 | United Kingdom . |

*Primary Examiner*—Michael L. Shippen
*Attorney, Agent, or Firm*—William G. Conger

[57] ABSTRACT

A process for the preparation of aliphatic, cycloaliphatic, arylaliphatic and aliphatic-cycloaliphatic di- and polyurethanes wherein primary aliphatic, cycloaliphatic, arylaliphatic or aliphatic-cycloaliphatic di- or polyamines are reacted with urea and a primary or secondary aliphatic alcohol at temperatures of above 190° C. to 300° C., following which ammonia and other by-products are separated from the aliphatic, cycloaliphatic, arylaliphatic or aliphatic-cycloaliphatic di- or polyurethane product.

18 Claims, No Drawings

PROCESS FOR THE PREPARATION OF ALIPHATIC DI- AND POLYURETHANES

This is a continuation-in-part application of co-pending application Ser. No. 135,247, filed on Mar. 31, 1980, which is expressly incorporated herein by reference, and which claims priority to Federal Republic of Germany application No. DE 2917493, filed Apr. 30, 1979.

BACKGROUND OF THE INVENTION

1. Field of the Invention

The invention pertains to the preparation of aliphatic, cycloaliphatic, arylaliphatic and aliphatic-cycloaliphatic N-substituted di- and polyurethanes by reacting primary aliphatic, cycloaliphatic, arylaliphatic or aliphatic-cycloaliphatic di- or polyamines with urea and alcohol.

2. Description of the Related Art

On an industrial scale, N-substituted urethanes are normally produces by the reaction of alcohols with isocyanates or by the reaction of amines with chlorocarbonates. The isocyanates and chlorocarbonates used in these reactions are obtained by phosgenation of the corresponding amines or alcohols. Houben-Weyl, *Methods of Organic Chemistry*, Vol. 8, pages 137, 120 and 101, (Georg Thieme Publishers, Stuttgart, 1952). These processes are very expensive and phosgene must be used with care because of its potential danger to man and the environment.

N-substituted urethane are used as both intermediates and end products. For instance, German Published Application No. 26 35 490 and U.S. Pat. No. 3,919,278 disclose the use of N-substituted urethanes for the manufacture of isocyanates. Because of their utility, many attempts have been made to develop better methods for preparing N-substituted urethanes. These methods and their shortcomings will be discussed in detail in the paragraphs which follow.

German Published Application No. 21 60 111 describes a process for the manufacture of N-substituted urethanes by reacting an organic carbonate with a primary or secondary amine in the presence of a Lewis acid. There are several problems with this process. The conversion rates are rather low, the reaction times are long, and N-alkylarylamines are always produced as by-products. Furthermore, the organic carbonate starting materials are themselves prepared from phosgene, and thus this process does not achieve the goal of a phoshene-free urethane preparation.

R. A. Franz et al, *Journal of Organic Chemistry*, Vol. 28, page 585 (1963) describe a process for making methyl-N-phenyl urethane from carbon monoxide, sulfur, aniline, and methanol. However, very low yields are produced by this method; the yield does not exceed 25 percent even when there is a long reaction period.

U.S. Pat. No. 2,409,712 discloses a method of preparing monoisocyanates by the pyrolysis of N-substituted urethanes, A process for making N-alkyl- and N-aryl-urethanes by the reaction of monoamines with urea and alcohol at temperatures of from 150° C. to 350° C. under increased pressure is disclosed. However, the disclosure describes only the manufacture of N-alkylmonourethanes and does not disclose the manufacture of N,N'-disubstutited diurethanes or poly-N-polysubstituted polyurethanes. The patent further discloses that the process is not suitable for all N-substituted urethanes. Furthermore, the yields disclosed are quite low and certainly unacceptable for commercial application.

U.S. Pat. No. 2,677,698 also describes a process for the manufacture of N-substituted monourethanes. In this process, urea is initially converted into the corresponding N,N'-disubstituted urea by reacting urea with a monoamine. The N,N'-disubstituted urea is then purified and reacted with an alcohol. The processes described are expensive and the yields are very low. Furthermore, the reaction is very slow, resulting in excessive reaction times. Attempts to improve the yield by improving the methods of preparing and purifying the N,N'-disubstituted ureas have not been successful.

A process similar to that mentioned in U.S. Pat. No. 2,409,712 is disclosed in U.S. Pat. No. 2,806,051. In this process, N-substituted urethanes are produced by reacting alkyl- or aryl-monoamines with urea and alcohol at a mole ratio of 1.0:1.2:2.0, preferably at temperatures of from 120° to 175° C., more preferably from 125° C. to 160° C. Even within the most preferably used temperature range, this process produces only small yields of N-substitued urethanes if the reaction time is limited to a period which is practical in an industrial setting.

The processes of U.S. Pat. Nos. 2,409,712 and 2,806,051 preferably take place below 160° C. The reason for this preference for low temperatures is presumably the tendency for urea and substituted ureas to react to form biurets and other products at higher temperatures. For example, urea is known to condense to form biuret and cyanuric acid at temperatures of from 150° to 175° C. Erickson, in *J. Am. Chem. Soc.* 76, 3977–78, showed that alkyl amines react with urea at lower temperatures, i.e 160° to 165° C., to produce mono- and di-substituted ureas while at a higher temperature of 170° to 200° C., monosubstituted and 1,3-disubstituted biurets were formed. For these and other reasons, the use of higher temperatures in reactions involving urea, and especially urea and amines, has been avoided.

In view of the problems disclosed in U.S. Pat. Nos. 2,409,712 and 2,806,051 with respect to yields and reaction times, it is no wonder that future attempts to produce N-alkylurethanes have not involved the reaction between amines, urea, and alcohol. The inventors of U.S. Pat. No. 3,076,007, for example, in searching for a commercially viable, non-phosgene approach to N-substituted monourethanes describe the N-alkyl, N-alkoxylalkyl and N-alkoxyalkoxyalkyl monourethanes of U.S. Pat. No. 2,409,712 as requiring phosgene for their preparation due to the fact that the available non-phosgene methods produce poor yields with numerous side reactions.

It is thus surprising that aliphatic, cycloaliphatic, and aliphatic-cycloaliphatic N-substituted di- and polyurethanes can be produced in a single process with good yields by reacting a diamine with urea and alcohol at higher temperatures, preferably temperatures of from greater than 190° C. to 300° C., and most preferably from 195° C. to 250° C. Prior teachings indicate that diureas and polyureas are obtained from diamines and urea; for example, hexamethylenediurea is obtained from hexamethylenediamine and urea. The prior art also teaches that, although urea and alcohol may react to produce urethanes, they continue to react to form N,N'-disubstituted ureas in the presence of amines. See Houben-Weyl, *Methods of Organic Chemistry*, Vol. 8, pages 151 and 140, (Georg Thieme Publishers, Stuttgart, 1952). These side reactions decrease the yield of the desired product.

None of the references cited discloses the preparation of aliphatic, cycloaliphatic, arylaliphatic or aliphatic-cycloaliphatic N-substituted di- and polyurethanes by reacting diamines or polyamines with urea and alcohol. Neither do the references disclose the unexpectedly high yields obtainable at higher temperatures. The reaction temperatures utilized in U.S. Pat. No. 2,806,051, for example, are low and only monoamines are used in this process. If diamines are used under these process conditions, one obtains high yields of a polymeric precipitate with a polyurea structure similar to the polyureas which are formed from diamines and polyisocyanates.

The use of higher temperatures for the reaction between diamines, urea, and alcohol is neither taught nor suggested in the prior art. As a matter of fact, the prior art suggests that higher temperatures should be avoided, as the patent and non-patent literature is replete with examples wherein diamines and urea participate in numerous reactions at higher temperatures yielding substituted biurets or a variety of other by-products; or participate in condensation reactions at higher temperatures to form polyurea thermoplastics.

For example, German Patent 896 412 indicates that high molecular weight, spinnable condensation products may be produced from the reaction of diamines with urea or other diamides of carbonic acid. This result is likely to occur if the amino groups of the diamines are separated by a chain of more than three atoms. Preparation of polyureas is taught in many other references also. In Great Britain Pat. No. 530,267, for example, urea reacts with aliphatic diamines in the presence of aromatic alcohols such as phenol and m-cresol at temperatures of from 100° to 270° C. High molecular weight polyureas are the product of this reaction. In U.S. Pat. No. 2,973,342, urea and diamines are reacted in the presence of water to form spinnable polyurea condensates at temperatures of from 130° C. to 200° C. U.S. Pat. No. 3,412,072 discloses the preparation of polyurea themoplastics by reacting diamines with urea in the presence of aliphatic alcohols such as ethanol and isopropanol at temperatures from 90° to 300° C.

In addition to the expected reaction of diamines with urea to form polyureas, any diurethanes formed may further react with unreacted diamine to form polyureas. For example, U.S. Pat. No. 2,181,663 and U.S. Pat. No. 2,568,885 disclose that high molecular polyureas with molecular weights of 8000 to 10,000 and greater, may be produced when diurethanes are condensed with diamines at temperatures of approximately 150° C. to 300° C. Moreover, as mono-, di-, and polyurethanes can be split thermally into isocyanates, alcohols, olefins, carbon dioxide, ureas, and carbodiimides, these products can further react to form numerous by-products such as biurets, allophanates, isocyanurates, and polycarbodiimides, among others. See *The Journal of the American Chemical Society*, Vol. 80, page 5495 (1958) and Vol. 48, page 1946 (1956).

In view of the problems disclosed in the prior art and the many possible side reactions, particularly polyurea formation, it was surprising that the process of the subject invention, which involves similar reaction conditions, would result in N-substituted di- and polyurethanes with excellent yields and in exceptional purity.

SUMMARY OF THE INVENTION

The object of the invention is to produce aliphatic, cycloaliphatic, arylaliphatic or aliphatic-cycloaliphatic, N-substituted di- and polyurethanes from readily available raw materials, under economically justifiable conditions, and with good yields. A further object is the avoidance of the use of catalysts and of strongly toxic raw materials such as phosgene, carbon monoxide, which are toxic themselves, or which form toxic compounds during the reaction.

These and other objects of the invention were unexpectedly net by developing a process for the preparation of aliphatic, cycloaliphatic, arylaliphatic, or aliphatic-cycloaliphatic N-substituted di- and polyurethanes comprising the steps of:

A. reacting a primary aliphatic, cycloaliphatic, arylaliphatic or aliphatic-cycloaliphatic primary di- or polyamine with urea and a primary or secondary aliphatic alcohol at temperatures of from greater than 190° C. to 300° C., and B. separating the ammonia and other by-products from the aliphatic, cycloaliphatic, arylaliphatic, or aliphatic-cycloaliphatic N-substituted di- and polyurethanes.

A further unexpected discovery was that a multiple step reaction wherein the alcohol to amino group ratio is increased in the second step from a lower initial value would result in a large decrease in overall reaction time. This decreased reaction time greatly enhances the commercial feasibility of the process.

The reaction may be illustrated by the following equation:

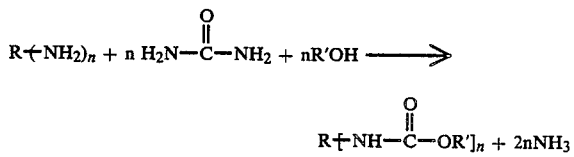

$$R(NH_2)_n + n\,H_2N-\overset{O}{\underset{\|}{C}}-NH_2 + nR'OH \longrightarrow$$

$$R[NH-\overset{O}{\underset{\|}{C}}-OR']_n + 2nNH_3$$

wherein R is an aliphatic, cycloaliphatic, arylaliphatic or aliphatic-cycloaliphatic residue of valence n, wherein n is 2 or greater, and wherein R' is a primary or secondary aliphatic, cycloaliphatic, or arylaliphatic residue of valence 1.

The aliphatic, cycloaliphatic, arylaliphatic, or aliphatic-cycloaliphatic N-substituted di- and polyurethanes produced according to the process of this invention are valuable as both end and intermediate products. The end products are frequently used, for instance, as pesticides. As intermediate products, they are frequently used as components for polycondensation reactions in polymer systems, and in particular, as feedstock to be pyrolyzed into the corresponding di- and polyisocyanates by splitting off the alcohol. The di- and polyisocyanates can be used in the manufacture of polyurethanes.

DESCRIPTION OF THE PREFERRED EMBODIMENTS

In order to prepare the aliphatic, cycloaliphatic, arylaliphatic, or aliphatic-cycloaliphatic N-substiuted di- and polyurethanes in accordance with the process of this invention, one or more primary aliphatic, cycloaliphatic, arylaliphatic or aliphatic-cycloaliphatic di- or polyamines and a primary or secondary aliphatic, cycloaliphatic, or arylaliphatic alcohol are reacted with urea in such quantities tities that the mole ratio of amino groups of the amine to urea to hydroxyl groups of the alcohol is 1:0.7–10:1–50, preferably 1:0.9–5:1–20 and in particular, 1:1–1.5:2–10.

The reaction preferably is carried out in the presence of excess alcohol at temperatures of from greater than 190° C. to 300° C. under reduced or elevated pressure. It has proven to be advantageous to remove the resultant ammonia from the reaction mixture as it is formed, for instance, by means of fractional distillation.

One or more catalysts may be added to the reaction mixture in order to increase the reaction rate. However it is preferred to carry out the reaction in the absence of catalysts so as to avoid later and possibly expensive catalyst removal. If catalysts are desired, it is preferrable to use insoluble, supported catalysts which do not contaminate the product mixture and whose later removal is then not necessary.

Primary amines having the formula $R—(NH_2)_n$ are well suited for the reaction with urea and alcohols according to this invention. In the aforementioned formula, R represents a multivalent, optionally substituted, aliphatic, cycloaliphatic, arylaliphatic or aliphatic-cycloaliphatic radical or mixed radical of this type; and n stands for a whole number, the value of which corresponds to the valency of R and is at least 2, preferably 2 to 5, and particularly 2. It is important that the amino groups be aliphatic primary amino groups. Thus the nature of the intervening linkages between the aliphatic amino groups may vary widely as will be presently discussed.

The aliphatic radicals contain 2 to 20, preferably 3 to 16, and particularly 4 to 12, carbon atoms. The aliphatic radicals may have a straight chain or branched structure, and may contain interspersed heteroatoms such as oxygen, sulfur or tertiary nitrogen atoms, or bivalent heterocyclic radicals as bridge members in bonded form. The cycloaliphatic radicals contain 5 to 12, preferably 6 to 12, carbon atoms whereas the mixed radicals of this type contain 8 to 50, preferably 10 to 15, carbon atoms. Representative examples of suitable diamines include: aliphatic diamines such as ethylenediamine, 1,3- and 1,2-propanediamine, 2,2-dimethyl-1,3-propanediamine, 1,4-butanediamine, 1,5-pentamethylenediamine, 1,6-hexamethylenediamine, 2,2,4-trimethyl-1,6-hexamethylenediamine, 1,8-octamethylenediamine, 1,10-decylenediamine, and 1,12-dodecylenediamine; cycloaliphatic diamines such as 1,2-, 1,3- and 1,4-cyclohexanediamine, 2,4- and 2,6-hexahydrotoluenediamine, as well as the corresponding isomer mixtures; aliphatic-cycloaliphatic diamines such as 1,4-hexahydroxylenediamine, 4,4'-, 2,4'- and 2,2'-diaminodicyclohexylmethane as well as the corresponding isomer mixtures, 2,2-bis(4-aminocyclohexyl)-propane, 3-aminomethyl-3,5,5-trimethylcyclohexylamine; dicyclopentadienyl compounds having the formula

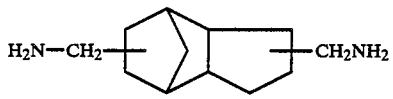

polyamines such as polycyclohexylpolymethylene polyamines having the formula

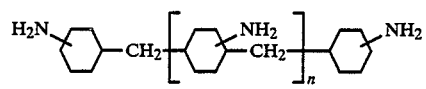

wherein n is a whole number generally from 1 to 4; and diamine mixtures containing mixtures of diaminodicyclohexylmethanes and polycyclohexylpolymethylenepolyamines and di- and polyamines containing heteroatoms or heterocyclic radicals in bonded form such as 3,3'-diaminodipropyl ether, or possibly substituted N,N'-bis(aminoalkyl)piperazines, for instance, N,N'-bis(2,2-dimethyl-3-aminopropyl)piperazine and N,N'-bis(aminopropyl)piperazine.

Arylaliphatic diamines useful in the process of the subject invention includes xylylenediamine, aryl-substituted xylylenediamines, α, β-dimethylxylylenediamine, and α, α, β, β-tetramethylxylylenediamine. Other arylaliphatic diamines wherein the amino groups are separated from the aromatic ring by at least one aliphatic carbon are also suitable.

Preferably used as amines are 1,6-hexamethylene diamine, 2,2,4-trimethyl-1,6-hexamethylenediamine, 1,4-hexahydroxylenediamine, 2,4- and 2,6-hexahydrotoluenediamine and their corresponding isomer mixtures, 4,4'-diaminodicyclohexylmethane, 1,4-diaminocyclohexane, 2,2-bis(4-amino-cyclohexyl)propane and 3-aminomethyl-3,5,5-trimethylcyclohexylamines.

Substituted or unsubstituted primary or secondary aliphatic alcohols and aromatic-aliphatic alcohols, as well as mixtures thereof, may be used as alcohols for the process according to this invention. Examples include primary aliphatic monoalcohols having 1 to 20 carbon atoms, preferably 1 to 10 carbon atoms, such as methanol, ethanol, propanol, n-butanol, isobutanol, 2- and 3-methylbutanol, neopentyl alcohol, pentanol, 2-methylpentanol, n-hexanol, 2-ethylhexanol, n-heptanol, n-octanol, n-nonanol, n-decanol, n-dodecanol, 2-phenylpropanol and benzyl alcohol; and secondary aliphatic and cycloaliphatic monoalcohols having 3 to 15 carbon atoms, preferably 3 to 6 carbon atoms, such as isopropanol, sec-butanol, sec-isoamyl alcohol, cyclopentanol, cyclohexanol, 2-, 3- or 4-methylcyclohexanol, and 4-tertiarybutylcyclohexanol. Preferably used are the monoalcohols methanol, ethanol, propanol, butanol, isobutanol, 2- and 3-methylbutanol, 2-ehtylbutanol, pentanol, 2-methylpentanol, hexanol, 2-ethylhexanol, heptanol, octanol, and cyclohexanol.

The reaction is preferably carried out with excess alcohol so that the alcohol functions as both a reaction component and simultaneously as a solvent. Instead of alcohol alone, however, mixtures of alcohols and other organic solvents which are inert under the reaction conditions may also be used as solvents.

According to this invention, the aliphatic, cycloaliphatic, arylaliphatic, and aliphatic-cycloaliphatic N-substituted di- and polyurethanes, preferably the diurethanes, may be produced in the absence of catalysts since the reaction normally takes place in economically acceptable reaction times and with good yields. This avoids costly purification operations for removing the catalysts from the resultant end products. However, suitable catalyst may be used if desired.

The one-step reaction takes place at temperatures higher than 190° C. up to about 300° C. as an upper limit, perferably from about 195° C. to 250° C., and particulary from about 195° C. to 230° C.; at pressures of 0.1 bar to 120 bar, preferably 0.5 bar to 60 bar, and in particular from 1 bar to 40 bar. The reaction times, which are appropriate for the corresponding temperature ranges, are from 0.1 hour to 50 hours, preferably 1 hour to 20 hours, and particularly 4 hours to 12 hours. With a given temperature, the reaction is preferably carried out under a pressure which allows the resultant ammonia to be fractionally distilled out of the reaction mixture. The appropriate conditions may readily be taken from physical character data tables for ammonia and alcohols.

The N-substituted di- and polyurethanes may be effectively prepared by mixing the reactants in the corresponding mole ratios, optionally in the presence of catalysts, in a pressurized or unpressurized reaction vessel equipped with a device for separating ammonia, and then heating the mixture for the appropriate amount of time. The resulting ammonia can be separated after the reaction has been completed. Preferably, however, it is separated as it is formed during the reaction by fractional distillation. It may be advantageous, particularly in the case of the reaction of low molecular weight alcohols under pressure, to separate the ammonia by using a stripping agent which is inert under the reaction conditions, such as nitrogen gas or the like.

A particularly advantageous method of preparing the di- and polyurethanes which, as a rule, results in a considerable reduction of the reaction time, is described as follows- (1) The primary aliphatic, cycloaliphatic, arylaliphatic, or aliphatic-cycloaliphatic di- or polyamine, urea, and alcohol are initially reacted, in a ratio of amino groups of the amine to urea to hydroxyl groups of the alcohol, of 1:1–1.5:1–2, preferably 1:1–1.25:1.25–1.75 for 1 hour to 4 hours, preferably 2 hours to 3 hours; (2) subsequently, additional alcohol is added to the reaction mixture in an amount such that 2.5 to 7.5, preferably 3 to 6 moles of alcohol are present per —NH$_2$ group of the amine and such that the reaction is completed in a total time period of from 4 hours to 20 hours, preferably 5 hours to 12 hours; and (3) the N-substituted di- or polyurethanes are isolated from the resulting reaction mixture either prior to or subsequent to separation of any catalyst or solid reaction products. This may be done, for instance, by completely and rapidly distilling off the alcohol and any solvent in addition to any small amounts of O-alkyl carbamates formed as by-products; by partially distilling off the alcohol and crystallizing the N-substituted di- or polyurethane; by preciptation by the addition of solvents in which the N-substituted di- or polyurethane is less soluble; or by transcrystallization from other solvents.

The quantities referred to in the examples which follow are in gram moles. The elementary molecular formulas and structures were confirmed by elementary analysis and mass spectrometry, in addition to infra-red and nuclear magnetic resonance spectra.

EXAMPLE 1

A reaction vessel is charged with 1.0 mole of 1,6-hexanediamine, 2.0 moles urea and 10.0 moles 1-octanol and agitated at a reflux temperature of from about 190° C. to 200° C. at normal pressure for 20 hours while ammonia is simultaneously removed by distillation. The reaction product crystallizes upon cooling of the reaction mixture. After filtration and drying, 0.91 mole of 1,6-bis(octoxycarbonylamino)hexane $C_{24}H_{48}N_2O_4$ is obtained (91 percent of theory relative to 1,6-hexanediamine). The melting point of the product is 108°–109° C.

EXAMPLE 2

In accordance with the procedure of Example 1, 1.0 mole 1,6-hexanediamine is reacted with 2.2 moles of urea and 10.0 moles of 1-octanol. The product obtained consists of 0.93 mole of 1,6-bis(octoxycarbonylamino)- hexane (93 percent of theory relative to 1,6-hexanediamine). The melting point of the product is determined to be 107°–109° C.

EXAMPLE 3

A reaction vessel is charged with 1.0 mole 1,6-hexanediamine, 2.2 moles urea, and 3.0 moles of 1-octanol, and agitated at a temperature of from about 190° C. to 200° C. for 10 hours. A quantity of insoluble solid material is removed by filtration from the reaction mixture after cooling to approximately 100° C. The mother liquor is allowed to crystallize by cooling to room temperatures and, after filtering, washing with 1-octanol and drying, 0.77 mole of 1,6-bis(octoxycarbonylamino)- hexane is obtained (77 percent of theory relative to 1,6-hexadiamine). The purity is approximately 95 percent and the melting point is 104°–106° C.

EXAMPLE 4

A reaction vessel is charged with 1.0 mole 1,6-hexanediamine, 2.2 moles urea, and 3.0 moles of 1-octanol, and agitated at a temperature of from about 190° C. to 200° C. for two hours. At that point, an additional 520 parts of 1-octanol is introduced into the reaction mixture and the reaction maintained for a period of eight hours. The reaction product crystallizes upon cooling. After filtering, washing with 1-octanol and drying, 0.96 mole of 1,6-bis(octoxycarbonylamino)hexane are obtained (96 percent theory relative to 1,6-hexamethylenediamine). The melting point if 107°–108° C.

EXAMPLE 5

A reaction vessel is charged with 2.0 moles of 1,6-hexanediamine, 4.4 moles urea, and 6.1 moles n-butanol, at a temperature of from about 190° C. to 195° C. and a pressure of 6 to 7 bar. Nitrogen is sparged into the reaction mixture via a dip tube, at a rate of 10 liters of nitrogen per hour per liter of reaction mixture. After approximately three hours, an additional 6.1 moles of n-butanol are added to the reaction mixture and the reaction is continued at 195° C. to 200° C. and 7 bar for 8 hours. By cooling the reaction mixture, the reaction product is allowed to crystallize. After filtering and recrystallizing from an acetone/water mixture, 1.88 moles of 1,6-bis(-butoxycarbonylamino)hexane are obtained (94 percent of theory relative to 1,6-hexanediamine). The melting point is 90°–92° C.

EXAMPLE 6

A reaction vessel is charged with 1.0 mole 1,6-hexanediamine, 2.0 moles of urea, and 2.8 moles ethanol and maintained at a temperature of from about 190° C. to 195° C. at a pressure of from about 23 bar to 25 bar for two hours. The reaction mixture is sparged with 7 liters of nitrogen per liter of reaction mixture an hour via a dip tube during this time. At this point, an additional 4.3 moles ethanol are added to the reaction mixture and the reaction is continued at from 195° C. to 200° C. for 8 hours. The reaction mixture is concentrated by distilling off the ethanol. The crystallized product is then filtered, and after recrystallization from an acetone/water mixture, 0.87 mole of 1,6-bis(ethoxycarbonylamino)hexane is obtained (87 percent of theory relative to 1,6-hexanediamine). The melting point is 80°–82° C.

EXAMPLE 7

A reaction vessel is charged with 1.0 mole of 4,4'-diaminodicyclohexylmethane, 2.2 mole urea, and 3.0 mole of 1-octanol and maintained at a temperature of from about 190° C. to 205° C. for two hours while ammonia is simultaneously removed by fractional distillation. At this point, an additional 3.9 moles of 1-octanol are introduced and the reaction is continued at a temperature of from about 195° to 210° C. for ten hours. The reaction mixture is cooled to 100° C. and solid impurities and/or by-products removed by filtration. The reaction mixture is allowed to crystallize by cooling to room temperature. After filtering, washing with 1-octanol and drying, 0.95 mole of 4,4'-bis(octoxycarbonylaminocyclohexyl)methane is obtained (95 percent of theory relative to 4,4'-diaminodicyclohexylmethane). The melting point is 129°–131° C. (recrystallized from ethyl acetate).

EXAMPLE 8

A reaction vessel is charged with 1.0 mole hexahydro-1,4-xylylenediamine, 2.1 moles urea, and 3.1 moles 1-octanol and maintained at a temperature of from about 190° to 200° C. for two hours while ammonia is simultaneously removed by fractional distillation. AT this point, 4.6 moles of 1-octanol are added to the reaction mixture and the reaction is continued at a temperature from about 195° C. to 210° C. for eight hours. Solid material is filtered from the reaction mixture, which is cooled to 110° C. The reaction product is allowed to crystallize by cooling to room temperature. After filtering, washing with 1-octanol, and drying, 0.96 mole of 1,4bis(octoxycarbonylaminomethyl)-cyclohexane is obtained (96 percent of theory relative to hexahydro-1,4-xylenediamine). The melting point is 122° C. (recrystallized from ethyl acetate).

EXAMPLE 9

A reaction vessel is charged with 1.0 mole 1,4-diaminocyclohexane, 2.0 moles urea, and 3.0 moles of 1-octanol and maintained at a temperature of from about 190° C. to 200° C. for three hours while ammonia is simultaneously removed by fractional distillation. After three hours, 4.7 moles of 1-octanol are added to the reaction mixture and the reaction is continued at a temperature of from about 195° C. to 210° C. for seven hours. The reaction product is allowed to crystallize upon cooling. After filtering, washing with 1-octanol and drying, 0.92 mole 1,4-bis(octoxycarbonylamino)cyclohexane is obtained (92 percent of theory relative to 1,4-diaminocyclohexane).

EXAMPLE 10

A reaction vessel is charged with 1.0 mole of 1.6-hexanediamine, 2.2 moles urea, and 5.4 moles 1,6-hexadecanol and maintained at 195° C. to 205° C. for 18 hours while ammonia is simultaneously removed by fractional distillation. The reaction mixture is allowed to cool, and approximately an equal volume of a mixture of ethanol and acetone (1/1) is added. Upon filtration, the filter cake consists of 0.63 mole 1,6-bis(hexadecoxycarbonylamino)hexane (63 percent of theory relative to 1,6-hexamethylenediamine). The melting point is 114°–116° C. (from ethyl acetate). The filtrate contains additional 1,6-bis(hexadecoxycarbonylamino)hexane.

EXAMPLE 11

A reaction vessel is charged with 1.0 mole 1,6-hexanediamine, 2.2 moles urea, and 3.0 moles of 2-butoxyehtanol and maintained at a temperature of from about 180° C. to 200° C. while ammonia is simultaneously removed by fractional distillation. Following this process, 5.5 moles of 2-butoxyethanol are added and the reaction is continued at reflux for eight hours. Unreacted butoxyethanol is removed by distillation in a water-jet vacuum, the residue is dissolved in methanol, and the product precipitated by adding water. After filtration and drying, 0.94 mole 1,6-bis(2-butoxyethoxycarbonylamino)hexane is obtained (94 percent of theory relative to 1,6-hexanediamine). The melting point is 64°–66° C.

EXAMPLE 12

A reaction vessel is charged with 1.2 moles of bis(3-aminopropyl)ether, 2.2 moles urea, and 3.0 moles of 1-octanol and maintained at a temperature of 185° C. to 200° C. for two hours while ammonia is simultaneously removed by fractional distillation. At this point, 4.7 moles of 1-octanol are added and the reaction is continued at reflux for six hours. Unreacted 1-octanol and by-product O-octyl-carbamate are distilled off up to a sump temperature of approximately 180° C. at 2 mbars pressure. Upon cooling, a crystallized residue is obtained consisting of 0.97 mole. bis(3-octoxycarbonylaminopropyl)ether, (97 percent of theory relative to bis(3-aminopropyl)ether). The purity is approximately 96 percent and the melting point is 61° C. (recrystallized from ethyl acetate).

EXAMPLE 13

A reaction vessel is charged with 1.0 mole 3-aminomethyl-3,5,5-trimethyl-1-aminocyclohexane, 2.0 moles urea, and 3.1 moles of 1-octanol and maintained at a temperature of from about 185° C. to 200° C. for two hours while ammonia is simultaneously removed by fractional distillation. At this point, 3.8 moles 1-octanol are added and the reaction is continued at reflux for ten hours. The reaction mixture is then quickly concentrated by means of distillation up to a sump temperature of approximately 200° C. at 2 mbars pressure. Obtained are 0.96 mole of 3-(octoxycarbonylaminomethyl)-3,5,5,-trimethyl-1-(octoxycarbonylamino)-cyclohexane as a partially crystallized residue (96 percent of theory). The purity is approximately 95 percent.

EXAMPLE 14

A reaction vessel is charged with 1.0 mole 1,6-hexanediamine, 2.0 moles urea, and 3.1 moles 2-ethylhexanol and maintained at a reflux temperature of from about 185° C. to 190° C. for three hours while ammonia is simultaneously removed by fractional distillation. At this point, another 6.2 moles 2-ethylhexanol is added and the reaction is continued at reflux for 15 hours. A quick distillation is conducted up to a sump temperature of 190° C. to 200° C. at 2 mbars pressure. The product, 445 grams of crude 1,6-bis(2-ethylhexoxycarbonylamino)hexane, is obtained as a slowly crystallizing residue. The purity is approximately 75 percent and the yield of pure product approximately 78 percent relative to 1,6-hexanediamine.

EXAMPLES 15 AND 16

In Examples 15 and 16, a reaction vessel (1000 ml autoclave) is charged with 1.1 mole 1,6-hexanediamine, 2.3 moles urea, and 6.6 moles n-butanol. The respective reaction mixtures are maintained at reflux temperatures of 200° C. and 210° C. by maintaining the pressure at 6.5 and 7.5 bar, respectively. Ammonia is removed simultaneously by means of a fractionating column. The yield of product, 1,6-bis(butoxycarbonylamino)hexane is analyzed by means of gel permeation chromatography. The yields are 0.79 mole and 1.03 moles, respectively, corresponding to yields of 72 percent and 94 percent based on 1,6-hexanediamine.

COMPARISON EXAMPLES

Comparison examples A and B were performed to illustrate the advantages of the subject invention over the process of U.S. Pat. No. 2,806,051. As previously discussed, one skilled in the art would expect diamines to react with urea in the presence of alcohol to produce high molecular weight polyurea thermoplatics. Comparison example A, which utilizes the reaction conditions and reactant ratios of U.S. Pat. No. 2,806,051, bears this out, yielding only polyhexamethylenepolyurea.

In Comparison Example B, the reactant conditions remain those of U.S. Pat. No. 2,806,051, but the reactant ratios were changed to correspond to those claimed in the process of the subject invention. Nevertheless, the sole product is again polyhexamethylenepolyurea.

In Comparison Example C, the raw materials and reactant ratios of subject invention Example 1 where followed, but a temperature near the upper end of the preferred range of U.S. Pat. No. 2,806,051 was utilized. Again, only polyhexamethylenepolyurea could be detected.

Comparison Example D shows that in order to achieve high yields with the one-step reaction of the subject invention, a temperature of above 190° C. must be utilized. Table I illustrates the dramatic decrease in yield which occurs at temperatures of about 190° C. and below as compared with that above 190° C.

COMPARISON EXAMPLE A

A reaction vessel is charged with 1.0 mole of 1,6-hexanediamine, 2.4 moles urea, and 2.0 moles n-butanol and maintained at 120° C. to 150° C. and 1 bar to 3 bars for a period of 20 hours. Considerable quantities of an amorphous solid material separate. The infrared spectrum (after filtering and drying) is virtually identical with the spectrum of poly(hexamethyleneurea). The material does not dissolve after heating in n-butanol at 190° C. and 6 bars to 7 bars for two hours. No 1,6-bis(butoxycarbonylamino)hexane could be isolated from the filtrate of the reaction mixture.

COMPARISON EXAMPLE B

A reaction vessel is charged with 1.0 mole 1,6-hexanediamine, 2.4 moles urea, and 11.3 moles n-butanol and maintained at reflux for 50 hours. During this time the reflux temperature slowly increases from 118° C. to 145° C. Large amounts of an amorphous solid precipitated. This solid is insoluble in the usual solvents and possesses an infrared spectrum virtually identical with polyhexamethylenepolyurea. No 1,6-bis(butoxycarbonylamino)hexane is detectable in either the filter cake or the filtrate.

COMPARISON EXAMPLE C

A reaction vessel is charged with 1.0 mole 1,6-hexanediamine, 2.0 moles urea, and 10.0 moles 1-octanol as in Example 1. The pressure is adjusted to maintain reflux at 150° C. over a period of 20 hours. Ammonia is removed by fractional distillation. A large quantity of an amorphous solid is separated by filtration. The infrared spectrum of this solid corresponds to that of a polyurea. No 1,6-bis (octoxycarbonylamino)hexane can be detected in either the filter cake or filtrate.

COMPARISON EXAMPLE D

The procedure of Examples 15 and 16 is used, but the temperature is maintained at 190°. The yield of 1,6-bis(butoxycarbonylamino)hexane is only 0.41 mole, corresponding to a 37 percent yield based on 1,6-hexanediamine.

TABLE I

| Example | Temperature (°C.) | Pressure (Bar) | Yield (%) |
|---|---|---|---|
| Comparison Example D | 190 | 5.5 | 37 |
| Example 15 | 200 | 6.5 | 72 |
| Example 16 | 210 | 7.5 | 94 |

The embodiments of the invention in which an exclusive privilege or property is claimed are as follows:

1. A process for the preparation of bis- or higher functional N-alkylcarbamates comprising:
    (a) reacting an aliphatic primary di- or polyamine with urea and a primary or secondary aliphatic alcohol in an amino-group to urea to alcohol ratio of from about 1:0.9:1 to 1:5:20 at a temperature of from in excess of 190° C. to about 300° C.; and
    (b) separating the bis- or higher functional N-alkyl carbamate product from unreacted and partly reacted starting materials, impurities, and by-products.

2. The process of claim 1 wherein said amino-group to urea to alcohol ratio is from about 1:1:2 to 1:1.5:10.

3. The process of claim 1 wherein said temperature is from about 195° C. to about 250° C.

4. The process of claim 2 wherein said temperature is from about 195° C. to about 250° C.

5. The process of claim 1 wherein said diamine is selected from the group consisting of 1,4-butanediamine, 1,6-hexanediamine, 1,8-octanediamine, 1,10-decanediamine, 1,12-dodecanediamine, 1,4-cyclohexanediamine, 3-aminomethyl-3,5,5-trimethyl-1-cyclohexaneamine, 1,4-bis(aminomethyl)-cyclohexane, 2-methyl-1,5-diaminocyclohexane, 2-methyl-1,3-diaminocyclohexane, 4,4'-diaminodicyclohexane, and 2,2'-,2,4'-, and 4,4'-diaminodicyclohexylmethane; and wherein said aliphatic alcohol is selected from the group consisting of methanol, ethanol, 1- and 2-propanol, 1- and 2-butanol, 1-hexanol, 1-octanol, 2-ethylhexanol, and cyclohexanol.

6. The process of claim 2 wherein said diamine is selected from the gropp consisting of 1,4-butanediamine, 1,6-hexanediamine, 1,8-octanediamine, 1,10-decanediamine, 1,12-dodecanediamine, 1,4-cyclohexanediamine, 3-aminomethyl-3,5,5-trimethyl-1-cyclohexaneamine, 1,4-bis(aminomethyl)-cyclohexane, 2-methyl-1,5-diaminocyclohexane, 2-methyl-1,3-diaminocyclohexane, 4,4'-diaminodicyclohexane, and 2,2'-, 2,4'-, and 4,4'-diaminodicyclohexylmethane; and wherein said aliphatic alcohol is selected from the group consisting of methanol, ethanol, 1- and 2-propanol, 1-and 2-butanol, 1-hexanol, 1-octanol, 2-ethylhexanol, and cyclohexanol.

7. The process of claim 3 wherein said diamine is selected from the group consisting of 1,4-butanediamine, 1,6-hexanediamine, 1,8-octanediamine, 1,10-decanediamine, 1,12-dodecanediamine, 1,4-cyclohexanediamine, 3-aminomethyl-3,5,5-trimethyl-1-cyclohexaneamine, 1,4-bis(aminomethyl)-cyclohexane, 2-methyl-1,5-diaminocyclohexane, 2-methyl-1,3-diaminocyclohexane, 4,4'-diaminodicyclohexane, and 2,2'-, 2,4'-, and 4,4'-diaminodicyclohexylmethane; and wherein said aliphatic alcohol is selected from the group consisting of methanol, ethanol, 1- and 2-propanol, 1- and 2-butanol, 1-hexanol, 1-octanol, 2-ethylhexanol, and cyclohexanol.

8. The process of claim 4 wherein said diamine is selected from the group consisting of 1,4-butanediamine, 1,6-hexanediamine, 1,8-octanediamine, 1,10-decanediamine, 1,12-dodecanediamine, 1,4-cyclohexanediamine, 3-aminomethyl-3,5,5-trimethyl-1-cyclohexaneamine, 1,4-bis(aminomethyl)cyclohexane, 2-methyl-1,5-diaminocyclohexane, 2-methyl-1,3-diaminocyclohexane, 4,4'-diaminodicyclohexane, and 2,2'-, 2,4'-, and 4,4'-diaminodicyclohexylmethane; and wherein said aliphatic alcohol is selected from the group consisting of methanol, ethanol, 1- and 2-propanol, 1- and 2-butanol, 1-hexanol, 1-octanol, 2-ethylhexanol, and cyclohexanol.

9. A multiple step process for the preparation of bis- or higher functional N-alkyl carbamates in shortened reaction time comprising:
(a) reacting in a first step an aliphatic primary di- or polyamine, urea, and a primary or secondary aliphatic alcohol in an amino-group to urea to alcohol ratio of from about 1:1:1 to about 1:1.5:2 at a temperature of from about 180° C. to about 300° C. for a period of from 1 to 4 hours;
(b) adding in a subsequent step sufficient alcohol to increase the alcohol to amino-group ratio to from about 2.5:1 to about 7.5:1, and continuing the reaction for a total time period of from 4 to 20 hours; and
(c) separating said bis- or higher functional N-alkyl carbamate product from unreacted and partly reacted starting materials, impurities and by-products.

10. The process of claim 9 wherein the amino-group to urea to alcohol ratio of step (a) is from about 1:1:1.25 to about 1:1.25:1.75; wherein the period of the reaction in step (a) is from about 2 to 3 hours; wherein the alcohol to amino-group ratio of step (b) is from about 3:1 to about 6:1; and wherein the total time period of the reaction is from about 5 hours to 12 hours.

11. The process of claim 9 wherein said temperature is from above 190° C. to about 300° C.

12. The process of claim 9 wherein said temperature is from about 195° C. to about 250° C.

13. The process of claim 9 wherein said diamine is selected from the group consisting of 1,4-butanediamine, 1,6-hexanediamine, 1,8-octanediamine, 1,10-decanediamine, 1,12-dodecanediamine, 1,4-cyclohexanediamine, 3-aminomethyl-3,5,5-trimethyl-1-cyclohexaneamine, 1,4-bis(aminomethyl)-cyclohexane, 2-methyl-1,5-diaminocyclohexane, 2-methyl-1,3-diaminocyclohexane, 4,4'-diaminodicyclohexane, and 2,2'-, 2,4'-, and 4,4'-diaminodicyclohexylmethane; and wherein said aliphatic alcohol is selected from the group consisting of methanol, ethanol, 1- and 2-propanol, 1- and 2-butanol, 1-hexanol, 1-octanol, 2-ethylhexanol, and cyclohexanol.

14. The process of claim 10 wherein said diamine is selected from the group consisting of 1,4-butanediamine, 1,6-hexanediamine, 1,8-octanediamine, 1,10-decanediamine, 1,12-dodecanediamine, 1,4-cyclohexanediamine, 3-aminomethyl-3,5,5-trimethyl-1-cyclohexaneamine, 1,4-bis(aminomethyl)cyclohexane, 2-methyl-1,5-diaminocyclohexane, 2-methyl-1,3-diaminocyclohexane, 4,4'-diaminodicyclohexane, and 2,2'-, 2,4'-, and 4,4'-diaminodicyclohexylmethane; and wherein said aliphatic alcohol is selected from the group consisting of methanol, ethanol, 1- and 2-propanol, 1- and 2-butanol, 1-hexanol, 1-octanol, 2-ethylhexanol, and cyclohexanol.

15. The process of claim 11 wherein said diamine is selected from the group consisting of 1,4-butanediamine, 1,6-hexanediamine, 1,8-octanediamine, 1,10-decanediamine, 1,12-dodecanediamine, 1,4-cyclohexanediamine, 3-aminomethyl-3,5,5-trimethyl-1-cyclohexylhexane, 1,4-bis(aminomethyl)-cyclohexane, 2-methyl-1,5-diaminocyclohexane, 2-methyl-1,3-diaminocyclohexane, 4,4'-diaminodicyclohexane, and 2,2'-, 2,4'-, and 4,4'-diaminodicyclohexylmethane; and wherein said aliphatic alcohol is selected from the group consisting of methanol, ethanol, 1- and 2-propanol, 1- and 2-butanol, 1-hexanol, 1-octanol, 2-ethylhexanol, and cyclohexanol.

16. The process of claim 12 wherein said diamine is selected from the group consisting of 1,4-butanediamine, 1,6-hexanediamine, 1,8-octanediamine, 1,10-decanediamine, 1,12-dodecanediamine, 1,4-cyclohexanediamine, 3-aminomethyl-3,5,5-trimethyl-1-cyclohexaneamine, 4-bis(aminomethyl)cyclohexane, 2-methyl-1,5-diaminocyclohexane, 2-methyl-1,3-diaminocyclohexane, 4,4'-diaminodicyclohexane, and 2,2'-, 2,4'-, and 4,4'-diaminodicyclohexylmethane; and wherein said aliphatic alcohol is selected from the group consisting of methanol, ethanol, 1- and 2-propanol, 1- and 2-butanol, 1-hexanol, 1-octanol, 2-ethylhexanol, and cyclohexanol.

17. The process of claim 1 wherein said unreacted and partly reacted starting materials and by-products are recycled.

18. The process of claim 9 wherein said unreacted and partly reacted starting materials and by-products are recycled.

* * * * *

UNITED STATES PATENT AND TRADEMARK OFFICE
CERTIFICATE OF CORRECTION

PATENT NO. : 4,713,476
DATED : December 15, 1987
INVENTOR(S) : FRANZ MERGER ET AL It is certified that error appears in the above-identified patent and that said Letters Patent is hereby corrected as shown below:

Column 14, claim 15, line 32, change -cyclohexylhexane to "-cyclohexaneamine."

Column 14, claim 16, line 45, change 4-bis to "1,4-bis."

Signed and Sealed this

Sixth Day of September, 1988

Attest:

DONALD J. QUIGG

Attesting Officer

Commissioner of Patents and Trademarks